(12) United States Patent
Agazzi

(10) Patent No.: US 9,430,849 B2
(45) Date of Patent: Aug. 30, 2016

(54) APPARATUS AND METHOD FOR PERFORMING AT LEAST ONE GEOMETRIC DIMENSION OF AN OBJECT

(71) Applicant: GEVIS SRL, Reggio Emilia (IT)

(72) Inventor: Giovanni Agazzi, Fidenza (IT)

(73) Assignee: GEVIS SRL, Fidenza (PR) (IT)

( * ) Notice: Subject to any disclaimer, the term of this patent is extended or adjusted under 35 U.S.C. 154(b) by 0 days.

(21) Appl. No.: 14/409,517

(22) PCT Filed: Jun. 17, 2013

(86) PCT No.: PCT/IB2013/054954
§ 371 (c)(1),
(2) Date: Dec. 19, 2014

(87) PCT Pub. No.: WO2013/190448
PCT Pub. Date: Dec. 27, 2013

(65) Prior Publication Data
US 2015/0199827 A1    Jul. 16, 2015

(30) Foreign Application Priority Data
Jun. 20, 2012 (IT) ................................ PR2012A0039

(51) Int. Cl.
| | |
|---|---|
| G06K 9/00 | (2006.01) |
| G06T 7/60 | (2006.01) |
| G01B 11/02 | (2006.01) |
| G01B 11/245 | (2006.01) |
| G01N 21/88 | (2006.01) |

(52) U.S. Cl.
CPC ............... *G06T 7/60* (2013.01); *G01B 11/02* (2013.01); *G01B 11/245* (2013.01); *G01N 21/88* (2013.01)

(58) Field of Classification Search
None
See application file for complete search history.

(56) References Cited

U.S. PATENT DOCUMENTS

| | | | | |
|---|---|---|---|---|
| 6,314,631 B1* | 11/2001 | Pryor | ................... | A01B 69/008 29/407.04 |
| 6,435,807 B1* | 8/2002 | Todorov | ................ | H01L 21/681 414/757 |
| 8,322,537 B2* | 12/2012 | Lindee | ................... | B25J 9/0093 209/592 |
| 2004/0085654 A1* | 5/2004 | Okazaki | ................. | G02B 27/26 359/819 |
| 2006/0182603 A1* | 8/2006 | Hawes | ................. | B25J 15/0253 414/735 |
| 2007/0127816 A1* | 6/2007 | Balslev | .................... | G06K 9/48 382/181 |

(Continued)

FOREIGN PATENT DOCUMENTS

| | | |
|---|---|---|
| EP | 0 872 724 A2 | 10/1998 |
| GB | 2 182 437 A | 5/1987 |

(Continued)

OTHER PUBLICATIONS

International Search Report, dated Oct. 10, 2013, from corresponding PCT application.

*Primary Examiner* — Hadi Akhavannik
(74) *Attorney, Agent, or Firm* — Young & Thompson

(57) ABSTRACT

Device and method for performing a measurement of at least one geometrical dimension of an object, where: a reference model of the object is acquired; the object is gripped by gripping elements (5) and a first image of the object is taken via optical elements (2); the object is translated and rotated in the three dimension by the gripping elements while images of the object are taken by the optical elements (2) until reaching a condition representative of the superimposition of the perimeter of the image of the object or of a portion of it with those of the reference model; then the measurement of the geometrical dimension is performed.

20 Claims, 4 Drawing Sheets

(56) References Cited

U.S. PATENT DOCUMENTS

| | | | | |
|---|---|---|---|---|
| 2008/0144922 A1* | 6/2008 | Naiki | ............... | G03F 9/7003 382/145 |
| 2009/0297316 A1* | 12/2009 | Wells | ............... | B66C 1/0212 414/737 |
| 2010/0172544 A1* | 7/2010 | Van Acker | ............... | C25C 3/06 382/106 |
| 2013/0156262 A1* | 6/2013 | Taguchi | ............... | G06T 7/0046 382/103 |

FOREIGN PATENT DOCUMENTS

| | | |
|---|---|---|
| WO | 2011/013153 A1 | 2/2011 |
| WO | 2011/121732 A1 | 10/2011 |

* cited by examiner

APPARATUS AND METHOD FOR PERFORMING AT LEAST ONE GEOMETRIC DIMENSION OF AN OBJECT

The present invention has as object a device and a method for measuring at least one geometric dimension (length of an arc, width of an angle, distance between two points, width of a radius etc.) of an object. Such device can have multiple applications, for example: controlling the wear of specific instruments or tools, discarding the non-compliant pieces etc.

Systems are known for measuring the size of a piece, which comprise means for positioning the piece with respect to a light source. The light source projects the shape of the object (possibly by means of a system of mirrors) on a work surface that is marked with a graduated scale for measuring distances. Before executing the measurements, the operator must correctly orient the object so as to ensure that defects of orientation with respect to that desired cannot ruin the projection of the shape on the work surface (and hence the measurement). For such purpose, the operator positions, on said work surface, a sheet that bears a technical drawing illustrating an orthogonal projection of the piece to be measured. The operator then superimposes said view and that projected on the work surface and manually adjusts the orientation of the piece until there is a complete overlap of the view reported on the sheet and the projected shape. At that point, by means of the graduated scale, the measurement is executed of the dimensions of interest.

One drawback of such solution is tied to the slowness of the operation of adjustment of the piece orientation for the purpose of obtaining a correct overlap of the projected image and the reference image designed on the sheet. In addition, such operation can be ruined by the ability of the operator or by the level of patience and precision of the same. Finally, it is necessary to obtain a specific support mechanics for the piece in order to maintain it in the desired position. This implies the availability of a considerable warehouse of mechanical elements, each necessary for the support of a specific object which must be measured.

An automatic method for the optical inspection of containers, in particular of the outer side wall of bottles, jars, vials etc. is described in the patent document WO2011/013153. The apparatus (and relative method) set the object of recognizing defects and in particular determining the integrity of the labels during the transportation of the containers along a conveyor belt, according to any one orientation angle that is unknown beforehand. The system first of all provides that the container to be inspected is provided with at least one three-dimensional reference axis, unequivocally defined and arranged in at least one optimal position, i.e. vertically with respect to the conveyor belt. The method provides for a rectification procedure on the surface of at least one lateral surface of the container based on two or more images acquired from a three-dimensional model of the container, such model stored in a memory unit. The method also provides for a step or procedure of calibration in which it comes to determine a relative spatial positioning of the telecameras with respect to the container on the belt, such container positioned in an optimal inspection position. In substance, the inspection chamber is traversed by a belt and a plurality of telecameras acquire two or more images of the conveyed container: the images are sent to the control and processing unit which executes the above-described optical inspection procedure.

Drawbacks of the art just described regard the fact that it will not be possible to adapt the position of the telecameras to that of the container; for example, if the container to be inspected had the revolution axis horizontally arranged with respect to the belt, the method would not be able to supply the desired inspection, if it does not provide for, as stated, a telecamera suitably arranged for plan view. In other words, the relative adaptation of the positioning between the viewing means and the means to be inspected (the container) will not be possible, if not by predefining possible arrangements thereof.

The same discussion can be made for the patent document EP872724, it too pertaining to a system of acquisition and inspection of containers in continuous advancement on conveyor belts, with random orientation but always with vertical revolution axis such that the container moving into the inspection zone is made to rotate with respect to said revolution axis by means of a mechanism constituted by a fixed wall and a movable belt, between which the containers are comprised, so as to produce the rotation thereof during the advancement on the conveyor. As stated above, drawbacks are tied to the need to have a symmetric container with defined rotation axis, and the mechanism only allows the rotation along said axis. In addition, the system has a functioning and requires a maintenance that are particularly complex. Here too, there is no system for automatically adapting the position of the piece to be inspected with respect to the telecameras.

Object of the present invention is to overcome the above-lamented drawbacks by providing the art with a device and a method that, by starting from a free object—i.e. with orientation/arrangement, with respect to the dimension to be measured, that is unknown beforehand—can automatically carry out the zeroing thereof (the adjustment of the orientation as a function of one or more references thereof identifiable beforehand) and the measurement of at least one geometric dimension of the object, overcoming the drawbacks of the prior art mentioned above. In such a manner, it is possible to increase the zeroing speed, the repeatability of the measurement and its execution precision.

Objects and advantages are therefore attained by the device and by the method comprising the technical characteristics set forth in one or more of the enclosed claims.

Further characteristics and advantages of the present invention will be clearer from the exemplifying and hence non-limiting description of a preferred but not exclusive embodiment of a device and method for measuring at least one geometric dimension of an object, as illustrated in the enclosed set of drawings in which.

Figure 2:
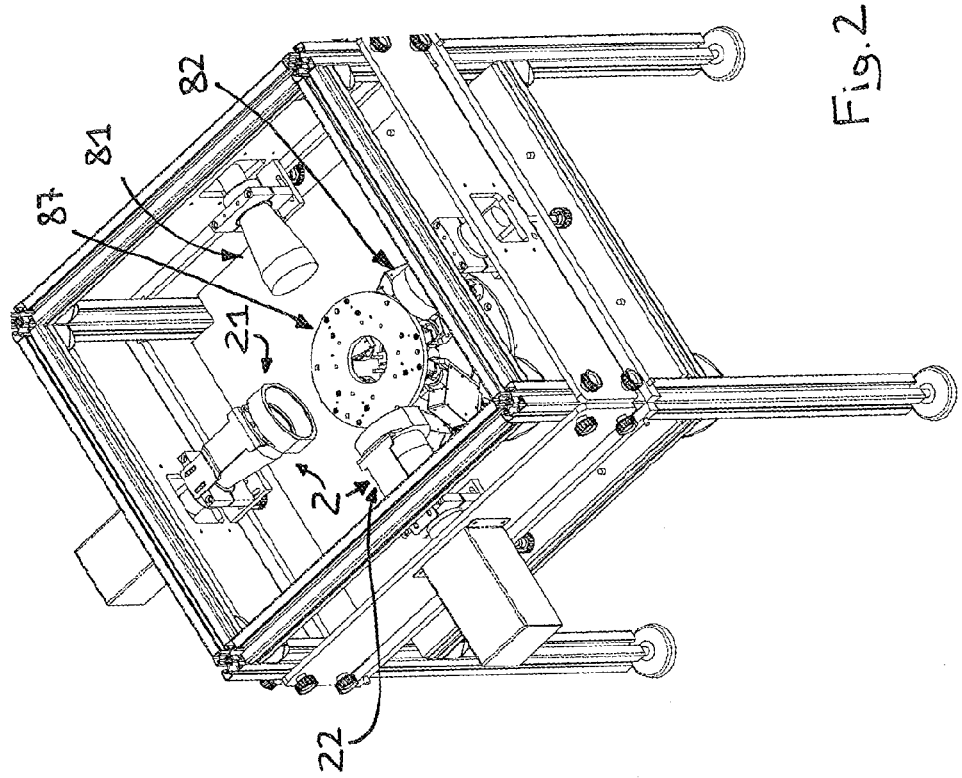
FIG. 2 illustrates a perspective view of part of a device according to the present invention.
Figure 1:
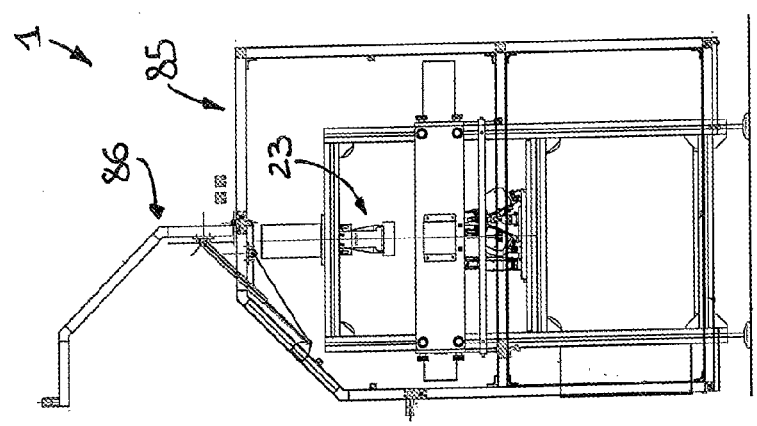
FIG. 1 illustrates a view of a device according to the present invention.
Figure 3:
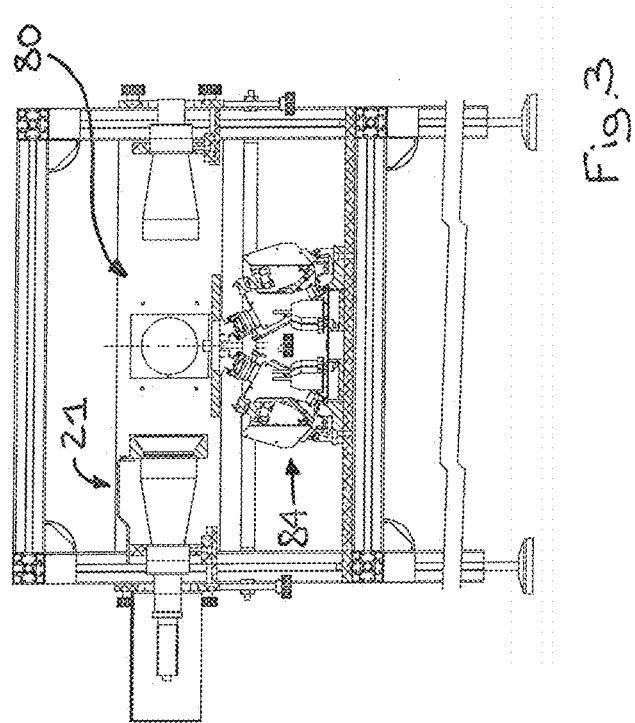
FIG. 3 and FIG. 5 show a vertical section view of the device of FIG. 2.
Figure 4:
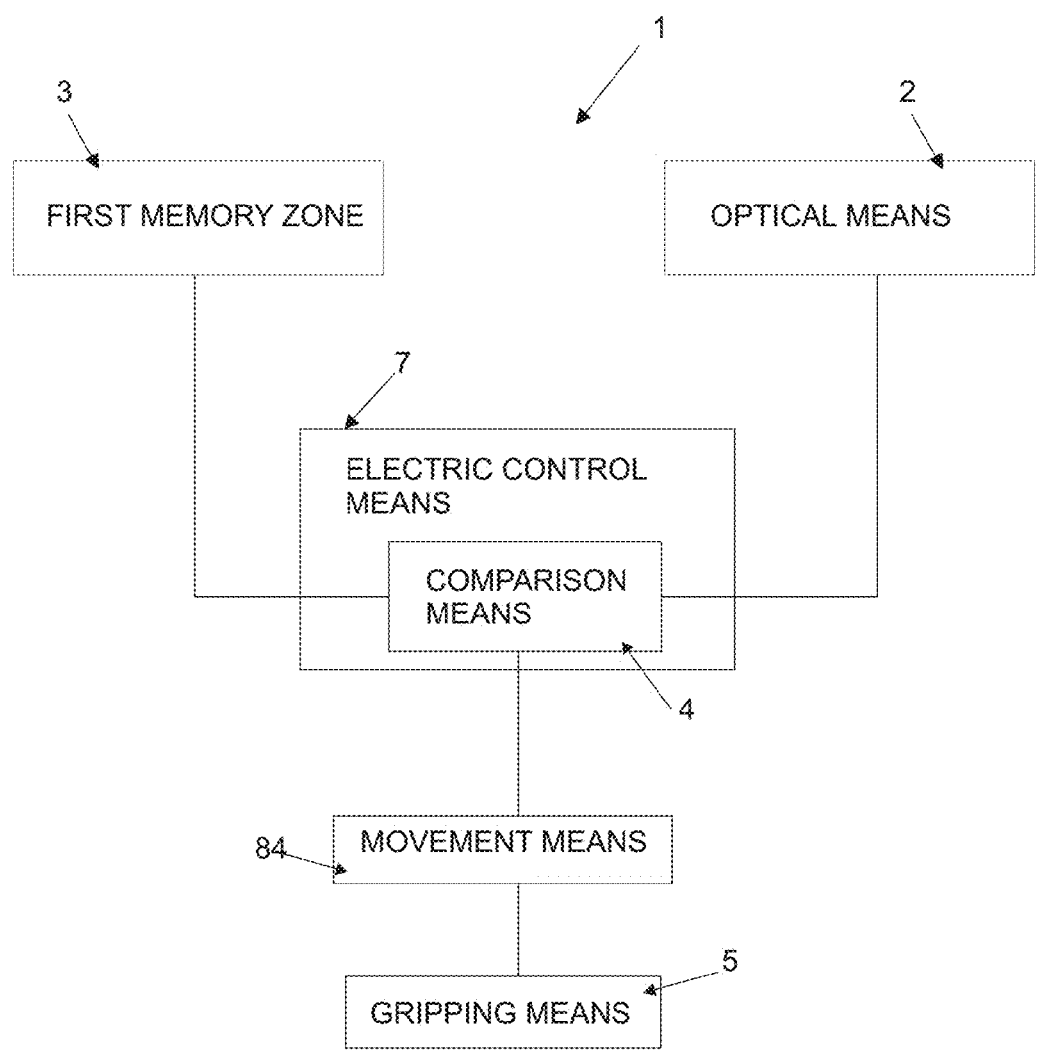
FIG. 4 shows a schematic block diagram of the device according to the present invention.
Figure 5:
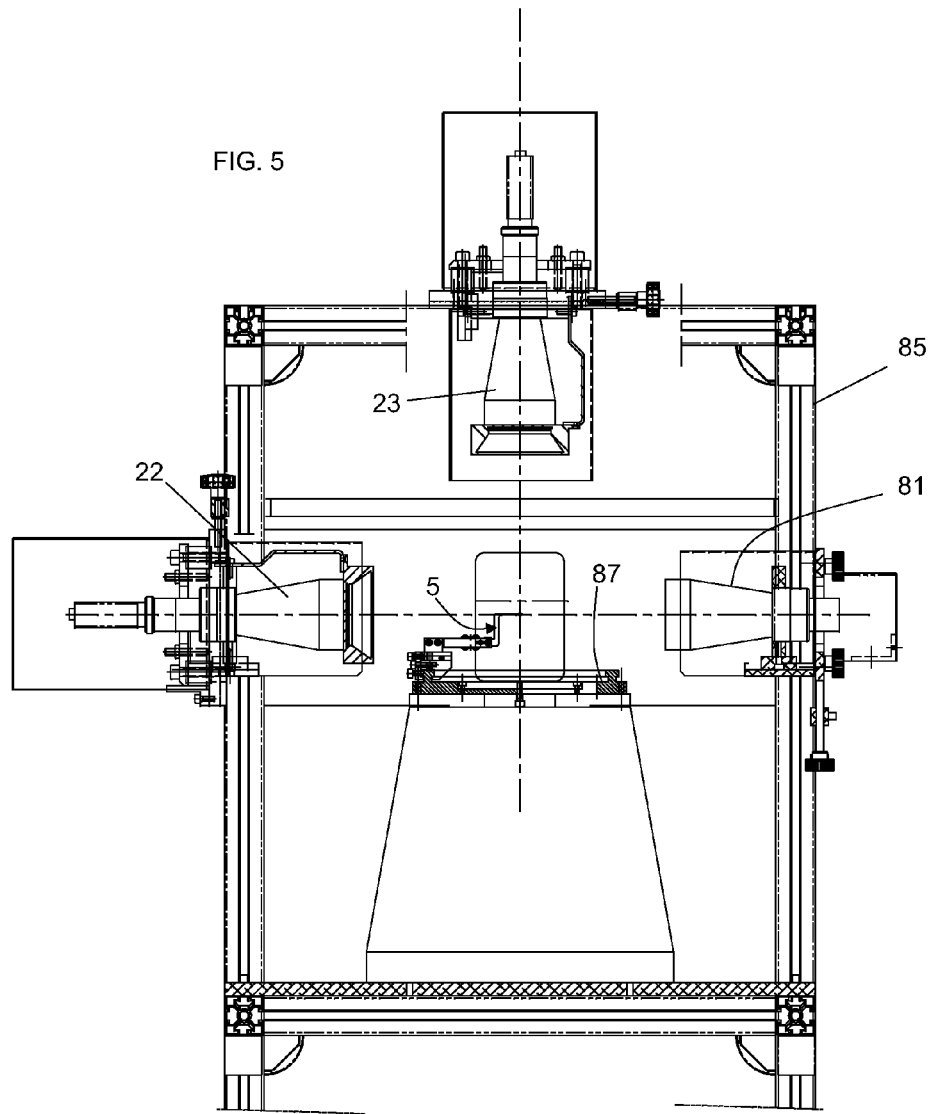

In the set of figures, the reference number 1 indicates a device for measuring a geometric dimension of an object, the latter not illustrated.

The device 1 comprises optical means 2 for detecting an image of the object to be measured. Such optical means 2 are of telecentric type.

Typically, such optical detection means 2 comprise at least one first camera or one first telecamera 21 (which thus allows detecting one or more shots or a continuous succession of images).

Preferably the optical detection means 2 comprise a second and a third camera or telecamera 22, 23. Advantageously the first and/or second and/or third camera or telecamera 21, 22, 23 are calibrated (for the purpose of generating pixel/millimeter transformation coefficients in a precise manner and recovering distortions of the lens, aberrations, magnifications, tilts etc. . . . ). This allows improving the precision of the measurement. The first, the second, the third camera or telecamera 21, 22, 23 are suitable for framing the object from three orthogonal directions. In the preferred solution, two telecameras or cameras (for example, in the set of figures the first and the second 21, 22) lie with the object on a same horizontal plane while one camera or telecamera (e.g. the third 23) is arranged above the object and frames it from above.

Suitably, the device 1 comprises means 5 for gripping the object.

Such gripping means 5 allow the positioning of the object in an operative zone 80 of the device 1 towards which the optical detection means 2 are directed.

Suitably, with reference to the indicated figures, the gripping means 5 comprise a gripper which in the specific case comprises two gripping arms and elastic means which exert an action of tightening of the arms. The use of such gripper is very advantageous, since with limited cost an element is provided that is capable of grasping a multiplicity of pieces (without requiring the obtainment of specific supports upon variation of the piece geometry). It is observed that the device 1 comprises first lighting means 81 that face the first telecamera or camera 21. The device 1 also comprises second lighting means 82 that face the second telecamera or camera 22. The device 1 also comprises third lighting means that face the third telecamera or camera 23 (not illustrated in the enclosed figures, but which illuminate the object from bottom to top). Suitably the first, second and third lighting means are telecentric.

The aforesaid operative zone 80 is at least partially interposed between the first telecamera or camera 21 and the first lighting means 81 (analogous considerations can be repeated for the operative zone 80 and the possible second camera or telecamera 22 and the second lighting means 82, as well as for the operative zone 80 and the third camera or telecamera 23 and the third lighting means).

That stated above signifies that the gripping means 5 are in any case at least partially interposed between the viewing means 21, 22, 23 (telecameras or cameras) and lighting means 81, 82, 83.

The first lighting means 81 and/or the second lighting means 82 and/or the third lighting means allow back lighting the object in a manner so as to highlight the perimeter shape of the object itself.

Possibly, the first camera or telecamera 21 (but it could also be repeated for the second and third camera or telecamera 22, 23) can also have a light source which if necessary allows lighting the object from a different point in order to highlight details thereof (in this manner, a frontal lighting of the object can be obtained).

According to a first embodiment, the device 1 comprises a first memory zone 3 in which a reference model of the sample is stored. Such model can be an image obtained from a software (e.g. in order to highlight the borders or several specific aspects) starting from a photograph or from a design of the sample. In such first memory zone 3, a first file can therefore be stored illustrating the reference model of the sample. In such case, the device 1 comprises means 4 for comparing the reference model and the images detected by the optical means 2 in order to allow the obtainment of a first condition.

In the first condition, a plurality of predetermined points of the reference model are superimposable on a plurality of corresponding predetermined points of an image detected in the first condition by means of optical means 2. The predetermined points are previously selected by the operator. Such predetermined points define references and their selection is closely tied to the distance of the piece that must be measured. In particular, in the first condition the edges of the reference model are superimposed on the edges of the image detected by the optical means 2.

The device comprises integrated electronic control means 7.

For such purpose, the electronic control means 7 control means 84 for moving the gripping means 5. The electronic control means 7 comprise an electronic control panel.

The means 84 for moving one or more gripping means 5 comprise a platform 87 to which said one or more gripping means 5 are constrained.

Typically the movement means 84 comprise a robot of hexapod type, such as the model M824 of the company "Phisik Instrumente", in brief a robot with six independent axes.

Suitably, the platform 87 supports the third lighting means (which are directed upward i.e. towards one of the cameras or telecameras of the optical means 2).

The gripping means 5 (in this embodiment identified by a gripper) are translatable along any one spatial direction and can rotate according to any one spatial rotation axis.

Such movements of the gripping means 5 are determined by the movement of the movement means 84 to which the gripping means 5 are constrained. Suitably, the device 1 comprises an external casing 85 comprising an access door 86 to said operative zone 80.

The electronic control means 7 can implement various techniques, such as known pattern matching techniques. For such purpose, the electronic control means 7 (and in particular the comparison means 4) implement one of the following softwares: "Matrox" Imaging, "Cognex" Patmax or "Dalsa" Sapera.

Advantageously, the first memory zone 3 could be integrated in the control means 7. In the preferred solution, it is the pattern matching software that allows the operator to select the predetermined points on the sample image.

Up to now, reference has been made to a particular method of object orientation with respect to a known model; nevertheless, without departing from the required protective scope, the comparison means 4 can implement other orientation techniques, taking as reference the object itself and its characteristics, such as for example:

a. The definition of the angle of one side of the object b. The definition of minimum value of one dimension (thickness) or maximum value (space between two walls, groove)

c. The definition of concentricity of a hole (inlet hole with respect to outlet hole).

The aforesaid variants, a, b, c, can be implemented and used, on their own or in combination, with other techniques or with those which take as reference a model as described above.

Object of the present invention is also a method for measuring a geometric dimension of an object retained by gripping means and not necessarily oriented by said means. As mentioned above, such dimension can for example be a radius, the length of a circumference, the distance between two points, the width of an angle etc. Suitably, but not necessarily, the method is implemented by a device 1 having one or more of the characteristics described above. The method advantageously comprises the step of acquiring a reference model of a sample with which the object is compared. The method in particular provides for storing said reference model in a first memory zone 3. The reference model is an image which shows characteristics of the sample.

The reference model typically illustrates the borders of the sample in accordance with a view point orthogonal to the plane along which it is desired to execute the measurement.

The method according to the present invention, before measuring the single pieces, therefore executes a preparatory sampling step.

Subsequently the method provides for the step of applying said object on gripping means 5.

The method also provides for the step of executing a detection of a first image of the object placed on the gripping means 5.

Orienting with respect to a known model is one of the possible options; alternatively or in combination, other techniques can be used such as:
 a. The definition of the angle of one side of the object
 b. The definition of minimum value of one dimension (thickness) or maximum value (space between two walls, groove)
 c. The definition of concentricity of a hole (inlet hole with respect to outlet hole).

In substance, the method provides for executing, after the detection of said first image, the verification of the position and if not aligned with that of the reference model, executing at least one relative movement and/or rotation of the optical acquisition means 2 and the gripping means 5 in order to attain a first condition such that the image provided by the optical means 2 is aligned with that of the reference model. The first condition is therefore a condition representative of the superimposition of the reference model perimeter and the perimeter of an image detected by the optical means 2 after one or more relative movements and/or rotations.

Said relative movement is provided along any one spatial direction and/or said rotation is provided according to any one spatial rotation axis.

With the described method, the self-alignment of the object to be measured with respect to at least one reference model of the sample is actuated in a completely automatic manner.

Preferably, during said relative movement (i.e. during the self-alignment), the optical means 2 are maintained still, whereas the gripping means 5 are moved. For such purpose, and as stated above, the means 84 for moving the gripping means 5 can translate along any one direction and/or rotate around any one axis.

In the first condition, the control means 7 identify an overlap between a plurality of predetermined points of an image detected by the optical means 2 and a plurality of predetermined points of the reference model of the sample.

In particular, the method provides that the user program the control means 7, indicating the predetermined reference points. In technical jargon, such points are also indicated as "zeroes".

Once the object on which it is desired to execute the measurements is in the first condition (defined above), the method provides for executing the actual measurement operation.

The measurement operation is implemented by a dedicated software of known type (e.g. Lippolis, triDmetrix, Messsosoftware M2, preferably MetroTool which is a known software developed by the same Applicant). Typically such measurement operation is executed by the control means 7. For example, the operator can select the distance between two points and possibly the trajectory along which such distance is measured.

For such purpose, the method provides for the step of executing a measurement of said at least one geometric dimension of the object by using an image detected in said first condition by the optical means 2.

In the preferred solution after the detection of the first image, the step for executing a relative movement of the optical means 2 and the gripping means 5 provides for implementing the following iterative procedure until the first condition is attained:
 executing a relative moment between the optical means 2 and the gripping means 5 which retain/grasp the object to be measured, said movement being controlled by the control means 7;
 executing, with the optical means 2, the detection of an image of the object placed on the gripping means 5, comparing it with the reference model in order to verify the attainment of the first condition.

The step of acquiring the reference model can comprise the step of detecting, by means of said optical means 2, an image of the sample placed on said gripping means 5.

Hence, the step of acquiring the reference model comprises the step of acquiring a photograph of the sample placed on the gripping means 5. For such purpose, it is advantageous to use the optical means 2 which are then also used in the subsequent step for detecting the images of the object on which it is desired to execute the measurement. Preferably the detected image of the sample can then be processed by a software in order to generate the reference model.

In an alternative solution, the step for acquiring the reference model comprises the step of storing, in the first memory zone 3 accessible by said control means 7, a file illustrating an image of the sample. Such file illustrates an image of the sample not detected through the optical means 2. Such file can be originated directly from the file in CAD format for the design of the piece itself (e.g. .dwg, .dxf or .bmp format) or other vector or bitmap formats.

The step for executing, after the detection of said first image, a relative movement of the optical acquisition means 2 and the gripping means 5 comprises a step for implementing pattern matching techniques by means of said control means 7. For such purpose the method provides for implementing, by means of the control means 7, a specific software such as one of those indicated above.

The invention thus conceived allows attaining multiple advantages.

In particular, it allows speeding up the measurement operations, in particular the preliminary steps before the measurement operations.

A further advantage is also linked to the increased repeatability of the measurement operation, which therefore is not dependent on the ability or the experience of an operator. A further important advantage is connected to the fact that one can use a single gripper for grasping pieces with different geometries.

The invention thus conceived is susceptible to numerous modifications and variants, all falling within the scope of the inventive concept characterizing it. In addition, all details can be substituted by other technically equivalent elements. In practice, all materials employed, as well as the sizes, can be of any type according to requirements.

In the embodiment, reference was made to gripping means 5 such as grippers; nevertheless, without departing from the required protective scope, technically equivalent elements can also be used in substitution of the grippers.

For example, gripping means 5 such as suckers, magnetic systems or other analogous devices can be used.

In any case, whatever means 5 are selected for retaining the object to be measured, this will be able to allow a translation or rotation movement, relative to the optical means 2, along any one direction/axis.

This allows being able to execute the zeroing step in a completely automatic manner; such step is the positioning of the object with respect to at least one reference model for the attainment of the ideal condition with which the requested measurement can then be executed.

The invention claimed is:

1. A method for automatically executing the measurement of at least one geometric dimension of an object having arrangement, with respect to the dimension to be measured, that is unknown beforehand, the method comprising:
   acquiring a reference model of a sample of the object positioned in a first condition, the reference model having a plurality of predetermined reference points;
   using a gripping means (5), gripping the object and moving the object within 3-dimensional space to attain the object being positioned in said first condition, the gripping means (5) providing movement of the object i) translatable along any one spatial direction and ii) rotatable around any one spatial rotation axis, wherein in moving the object to be positioned in the first condition, the gripping means being operatively controlled by an electronic control means (7) to repeatedly move the object from a current position to a new position using translation and rotation until the object is determined to be positioned in the first condition;
   with the object gripped by the gripping means (5) in the new position, using an optical means (2) to acquire an image of the object;
   using a comparison means (4) to compare i) the plurality of predetermined reference points of the reference model with ii) a plurality of corresponding predetermined reference points of the image of the object taken with the object in the new position, to determine whether the object is positioned in the first condition; and
   upon the comparison means (4) determining that the object is positioned in the first condition, using the electronic control means to make a geometric measurement of the object.

2. The method according to claim 1, wherein said first condition is identifiable with reference models/images and/or with the definition of a characteristic of the object such as an angle of one side, a minimum or maximum value of one dimension thereof, the concentricity of its holes.

3. The method according to claim 2, wherein the step of acquiring the reference model comprises the step of detecting, by means of said optical means (2), an image of the object placed on said gripping means (5).

4. The method according to claim 1, wherein the step of acquiring the reference model comprises the step of executing a photograph of the object through the optical means (2).

5. The method according to claim 1, wherein the step of acquiring the reference model comprises the step of storing a file in a first memory zone (3) accessible by said electronic control means (7), said file illustrating an image of the sample not detected through the optical means (2).

6. The method according to claim 1, wherein after the detection of said first image, the step of executing a relative movement of the optical acquisition means (2) and the gripping means (5) comprises the step of implementing, by means of said control means (7), pattern matching techniques.

7. A device (1) for automatically measuring at least one geometric dimension of an object with arrangement, with respect to the dimension to be measured, that is unknown beforehand; the device comprising:
   an electronic control means (7);
   a first memory zone (3) storing a reference model of a sample of the object positioned in a first condition, the reference model having a plurality of predetermined reference points, the first memory zone (3) being operatively connected to the electronic control means (7);
   a gripping means (5) that grips the object and moves the object within 3-dimensional space to attain said object being positioned in said first condition, said gripping means (5) being at least one of the group consisting of i) translatable along any one spatial direction and ii) rotatable around any one spatial rotation axis, said gripping means being operatively controlled by the electronic control means (7) from a current position to a new position;
   an optical means (2) that acquires at least one image of the object with the object having been positioned in the new position by the gripping means (5), the optical means (2) being operatively connected to electronic control means (7);
   a comparison means (4) that compares i) the plurality of predetermined reference points of the reference model with ii) a plurality of corresponding predetermined reference points of the at least one image of the object taken with the object having been positioned in the new position, to determine whether the object is positioned in the first condition,
   wherein upon the comparison means (4) determining the object is positioned in the first condition, the electronic control means makes a geometric measurement of the object.

8. The device according to claim 7, wherein the electronic control means (7) control a further means (84) for moving the gripping means (5); and the further means (84) for moving the gripping means (5) comprises a platform (87) to which said gripping means (5) is constrained.

9. The device according to claim 7, wherein,
   wherein the gripping means (5) is both i) translatable along any one spatial direction and ii) rotatable around any one spatial rotation axis,
   said optical means (2) is comprised of first, second, and third cameras or telecameras fixedly arranged to frame the object from three directions, the first camera or telecamera being oriented along a first direction in a first plane containing the object, the second camera or telecamera being oriented along a second direct in the first plane, and the third camera or telecamera being oriented above the first and second cameras along a second plane contains the object, and
   said comparison means compares images of the object, in the new position, from each of the three cameras or telecameras in determining whether the object is positioned in the first condition.

10. The device according to claim 7, wherein said gripping means (5) comprise at least one gripper.

11. The device according to claim 7, wherein said gripping means (5) comprise at least one magnetic retention system.

12. The device according to claim 7, wherein said gripping means (5) comprise at least one retention system with suckers or pneumatic vacuum.

13. The method according to claim 2, wherein the step of acquiring the reference model comprises the step of storing a file in a first memory zone (3) accessible by said control means (7), said file illustrating an image of the sample not detected through the optical means (2).

14. The device of claim 7, wherein the gripping means (5) is both i) translatable along any one spatial direction and ii) rotatable around any one spatial rotation axis.

15. The device of claim 14, wherein said optical means (2) is comprised of first, second, and third cameras or telecameras arranged to frame the object from three orthogonal directions, the first camera or telecamera being oriented along a first direction in a first plane containing the object, the second camera or telecamera being oriented along a second direct in the first plane, the second direction being orthogonal to the first direction, and the third camera or telecamera being oriented above the first and second cameras along a second plane contains the object, the second plane being orthogonal to the first plane, and said comparison means compares images of the object, in the new position, from each of the three cameras or telecameras in determining whether the object is positioned in the first condition.

16. The device of claim 14, wherein said optical means (2) is comprised of first, second, and third cameras or telecameras arranged to frame the object from three directions, the first camera or telecamera being oriented along a first direction in a first plane containing the object, the second camera or telecamera being oriented along a second direct in the first plane, and the third camera or telecamera being oriented above the first and second cameras along a second plane contains the object, and said comparison means compares images of the object, in the new position, from each of the three cameras or telecameras in determining whether the object is positioned in the first condition.

17. The device of claim 7, wherein said optical means (2) is comprised of first, second, and third cameras or telecameras arranged to frame the object from three orthogonal directions, the first camera or telecamera being oriented along a first direction in a first plane containing the object, the second camera or telecamera being oriented along a second direct in the first plane, the second direction being orthogonal to the first direction, and the third camera or telecamera being oriented above the first and second cameras along a second plane contains the object, the second plane being orthogonal to the first plane, and said comparison means compares images of the object, in the new position, from each of the three cameras or telecameras in determining whether the object is positioned in the first condition.

18. The method of claim 1, wherein,
said optical means (2) is comprised of first, second, and third cameras or telecameras fixedly arranged to frame the object from three directions,
the first camera or telecamera being oriented along a first direction in a first plane containing the object,
the second camera or telecamera being oriented along a second direct in the first plane, and
the third camera or telecamera being oriented above the first and second cameras along a second plane contains the object, and
said comparison means compares images of the object, in the new position, from each of the three cameras or telecameras in determining whether the object is positioned in the first condition and determines said measurement from said images.

19. The method of claim 1, wherein,
wherein said optical means (2) is comprised of first, second, and third cameras or telecameras fixedly arranged to frame the object from three orthogonal directions,
the first camera or telecamera being oriented along a first direction in a first plane containing the object, the second camera or telecamera being oriented along a second direct in the first plane,
the second direction being orthogonal to the first direction, and
the third camera or telecamera being oriented above the first and second cameras along a second plane contains the object, the second plane being orthogonal to the first plane, and
said comparison means compares images of the object, in the new position, from each of the three cameras or telecameras in determining whether the object is positioned in the first condition and determines said measurement from said images.

20. A method for automatically measuring an geometric dimension of an object, the method comprising:
acquiring a reference model of a sample of the object positioned in a first condition, the reference model having a plurality of predetermined reference points;
using a gripping means (5), self-aligning the object to be positioned in the first condition by gripping the object and repeatedly moving the object within 3-dimensional space until the object is determined to be positioned in the first condition, the gripping means (5) i) translating the object along any one spatial direction and ii) rotating the object around any one spatial rotation axis, wherein in moving the object to be positioned in the first condition, the gripping means is operatively controlled by an electronic control means (7) to repeatedly move the object from a current position to a new position using translation and rotation until the object is determined to be positioned in the first condition;
with the object gripped by the gripping means (5) in the new position, using an optical means (2) to acquire three images of the object, said optical means (2) being comprised of first, second, and third cameras or telecameras arranged to image the object from three directions, the first camera or telecamera taking a first of the three images and being oriented along a first direction in a first plane containing the object, the second camera or telecamera taking a second of the three images and being oriented along a second direct in the first plane, and the third camera or telecamera taking a third of the three images and being oriented above the first and second cameras along a second plane contains the object;
using a comparison means (4) to superimpose i) the plurality of predetermined reference points of the reference model with ii) a plurality of corresponding predetermined reference points of each of the three images of the object taken with the object in the new position, to determine whether the object is positioned in the first condition; and
upon the comparison means (4) determining that the object is positioned in the first condition, making a geometric measurement of the object using one of the three images of the object taken by the optical means with the object positioned in the first condition.

\* \* \* \* \*